(12) United States Patent
Adornetto et al.

(10) Patent No.: US 12,036,546 B2
(45) Date of Patent: Jul. 16, 2024

(54) SAMPLING DEVICE FOR A LIQUID SAMPLE

(71) Applicant: Feral GmbH, Berlin (DE)

(72) Inventors: Gianluca Adornetto, Berlin (DE); Eirini Rapti, Berlin (DE); Fabio La Manna, Berlin (DE); Franziska Mayer, Berlin (DE); Filip Von Hauswolff, Malmö (SE)

(73) Assignee: Feral GmbH, Berlin (DE)

( * ) Notice: Subject to any disclaimer, the term of this patent is extended or adjusted under 35 U.S.C. 154(b) by 189 days.

(21) Appl. No.: 17/084,491

(22) Filed: Oct. 29, 2020

(65) Prior Publication Data

US 2021/0129137 A1 May 6, 2021

(30) Foreign Application Priority Data

Oct. 30, 2019 (EP) ..................................... 19206130

(51) Int. Cl.
*B01L 3/00* (2006.01)
*G01N 21/77* (2006.01)

(52) U.S. Cl.
CPC ............ *B01L 3/5023* (2013.01); *G01N 21/77* (2013.01); *B01L 2300/0825* (2013.01); *G01N 2021/7759* (2013.01)

(58) Field of Classification Search
None
See application file for complete search history.

(56) References Cited

U.S. PATENT DOCUMENTS

| | | | |
|---|---|---|---|
| 2004/0171173 A1* | 9/2004 | Eckermann | B01L 3/5023 436/514 |
| 2008/0112848 A1* | 5/2008 | Huffstodt | G01N 21/8483 422/68.1 |
| 2008/0118397 A1 | 5/2008 | Slowey et al. | |
| 2009/0318829 A1* | 12/2009 | Hannant | B01L 3/5029 600/562 |
| 2013/0343955 A1* | 12/2013 | Doyle | B01L 3/5055 422/68.1 |
| 2018/0356413 A1* | 12/2018 | Parekh | A61M 1/287 |

FOREIGN PATENT DOCUMENTS

| | | |
|---|---|---|
| WO | 02097389 A2 | 12/2002 |
| WO | 2007099344 A1 | 9/2007 |
| WO | 2012163788 A1 | 12/2012 |
| WO | 2017178621 A2 | 10/2017 |

OTHER PUBLICATIONS

European Search Report cited in EP 19206130 dated Apr. 14, 2020.
"European Examination Report" mailed Jan. 17, 2023 cited in EP Application No. 19206130.7, 4 pages.

* cited by examiner

*Primary Examiner* — Lore R Jarrett
(74) *Attorney, Agent, or Firm* — Perkins Coie LLP; Jordan Becker

(57) ABSTRACT

The present disclosure relates to a sampling device for a liquid sample. The sampling device can comprise a main case and a sample transfer member that can be configured in a sample acquisition configuration and in a sample transfer configuration.

19 Claims, 7 Drawing Sheets

SAMPLING DEVICE FOR A LIQUID SAMPLE

TECHNICAL FIELD

The present disclosure relates to a sampling device for a liquid sample, a reading device, and a sampling system that includes a sampling device and a reading device.

BACKGROUND

Liquid samples are acquired and analyzed in a variety of technical fields. One major field is medicine, where liquid samples are acquired from a living organism, for example from a human body. In human medicine a variety of types of liquids can be sampled for a variety of different purposes.

For example, it is known to acquire a saliva sample using a stick with a pad. Such a stick can be stored in a transport container, such as a glass, for the purpose of transportation to a laboratory, where the saliva sample can be analyzed.

For analysis, the liquid sample can be applied to a test strip, for example. Such test strips are commonly known as lateral flow assays, for example.

However, the sampling equipment commonly known exposes the sample to the risk of contamination during transportation and handling. Further, the known equipment requires trained personnel to acquire, transport and analyze the liquid sample.

DETAILED DESCRIPTION

The following reference numerals and corresponding elements are used in this description:

10 sampling device
12 liquid sample
14 main case
16 clamping portion
18 sample reception section
20 indicator section
22 test strip mounting portion
24 test strip
26 sample transfer member
28 sample acquisition portion
30 sample acquisition configuration
32 sample transfer configuration
34 clamping element
36 operative connection
38 sliding movement
40 pivoting movement
44 operative connection
46 connection
48 proximal end
50 operative connection
52 operative connection
54 upper case
56 lower case
58 front section
60 back section
62 integral hinge
64 beak-like kinematics
66 window
68 base portion
70 sample handling portion
72 serial kinematics
74 integral hinge
76 pin connection
78 pad
80 strainer
82 guiding blades
84 handling nipple
86 elongated condition
88 rod-type structure
90 recess
92 snap-fit
94 structural elastic force
96 pressing force
98 shortened condition
100 pressing force
102 sampling system
104 reading device
106 result
108 mechanical interface
110 sensing unit Overview The present invention aims at providing improved sampling equipment for a liquid sample that is comfortable and safe in use.

This objective is achieved by the subject-matter of the independent claims 1, 14 and 15. Preferred embodiments of the present invention can be gained from the dependent claims and the description.

A first aspect of the invention refers to a sampling device for a liquid sample, comprising:

a) a main case having a clamping portion, a sample reception section and an indicator section, said sample reception section being located within said clamping portion, wherein said main case further has a test strip mounting portion designed to have a test strip mounted therein so that said test strip extends into said sample reception section as well as said indicator section; and b) a sample transfer member being connected to said main case and having a sample acquisition portion, wherein said sample transfer member and said main case are configurable in at least the following configurations:

i) a sample acquisition configuration, wherein said sample acquisition portion is located outside said main case and securable in said configuration by said clamping portion; and ii) a sample transfer configuration, wherein said sample acquisition portion is located within said sample reception section and securable in said configuration by said clamping portion.

The sampling device of the invention allows for safe and comfortable acquisition of a liquid sample by applying said sample acquisition portion in the sample acquisition configuration to a source of said liquid. Thus, said liquid sample is safely and comfortably transferred to said sample acquisition portion that is well accessible outside of said main case, while said sampling device can be handled safely with said sample acquisition portion being securable by said clamping portion.

To manipulate said sample transfer member and said main case from said sample acquisition configuration to said sample transfer configuration, said sample acquisition portion is given free by said clamping portion. To achieve said sample transfer configuration, said sample acquisition portion is moved, preferably while carrying said liquid sample, into said sample reception section. Therein, said sample acquisition portion is again securable by said clamping portion.

As a test strip, if mounted in said test strip mounting portion, extends into said sample reception section, said liquid sample is transferred from said source of said liquid to said sample reception section and can therein be brought in contact with said test strip. Since said test strip is also extending into said indicator section of said main case, a reaction of said test strip to said liquid sample can be observed in said indicator section, preferably from outside of said main case.

Based on that, the sampling device of the invention allows for comfortable and safe acquisition and fast processing of a liquid sample. Accordingly, the sampling device of the invention is in particular suitable for private users, however it is suitable for professional users as well.

The sampling device of the invention preferably has a size to have it comfortably used by hand. Preferably, it measures between 8 cm and 11 cm in length, depending on the current configuration. Preferably, it measures between 1 cm and 2 cm in width. Preferably, it measures between 0.4 cm and 0.6 cm in height.

For example, the sampling device of the invention can be delivered originally packed in a protecting case, for example a plastic foil and with a test strip mounted already in said sampling device. Upon delivery, said sampling device can have said sample acquisition configuration with said sample acquisition portion being secured, so as to allow for said sampling device being handled like a one-piece stick-type of device.

A user can unwrap said sampling device and apply said sample acquisition portion to his body or to that of a patient in order to acquire a liquid sample. For example, a saliva sample can be acquired applying said sample acquisition portion to a mouth of a user or patient.

Once said liquid sample is acquired, the user can untighten said clamping portion and manually move said sample acquisition portion along with said liquid sample into said sample reception section. Then, the user can again tighten said clamping portion to secure said sample acquisition portion with said liquid sample within said sample reception section. This shows, how fast and easy said liquid sample can be freshly acquired and freshly stored inside said sampling device, without any danger of decontaminating said liquid sample by environmental factors or of harming the environment by said liquid sample.

Since in said sample transfer configuration said liquid sample is brought into contact with said test strip, processing of said liquid sample starts automatically and a result can be comfortably gained from said indicator section.

Preferably, the sampling device of the invention is designed for single use. In that case, said sampling device can be easily and safely disposed as a unit after having gained the result. Preferably the sampling device of the invention is made of a plastics material.

Depending on the liquid to be sampled, the sample acquisition portion preferably comprises a pad suitable for the respective type of liquid. The sample acquisition portion allows for a temporary binding of the liquid sample for the purpose of transportation, but at least partially releases said liquid sample after said sample transfer member and said main case have been configured in the sample transfer configuration.

The at least partial release can preferably be realized by delayed off-dripping, further preferred by wetting another component inside said sample reception section and even further preferred by squeezing said liquid sample at least partially off the pad by said clamping portion.

It is mostly preferred to use a combination of wetting another component inside said sample reception section and of squeezing said liquid sample at least partially off said pad.

Said sample transfer member can be connected to said main case permanently or reversibly. Preferably, said sample transfer member is connected reversibly to said main case.

It shall be understood that said sample transfer member preferably is continuously moveable between said sample acquisition configuration and said sample transfer configuration and that it can have intermediate configurations, as well.

If said sample acquisition portion is to be secured in said sample acquisition configuration or in said sample transfer configuration, said clamping portion can be tightened. If said sample acquisition portion is to be set free again, said clamping portion can be untightened. The functionality of said clamping portion can be achieved by moving one or more clamping elements of said clamping portion. For example, a clamping element of said clamping portion can be moved in a slidable manner or in a pivoting manner, relatively to the main case. Preferably, said main case can be closed or opened by tightening or untightening said clamping portion.

Said sample acquisition portion is secured, if said clamping portion at least assures that said sample acquisition portion does not lose its current configuration, which means said sample acquisition portion remains outside said main case or within said sample reception section.

If said sample acquisition portion is secured in said sample transfer configuration, said main case is preferably closed. If said sample acquisition portion is secured in said sample acquisition configuration, said main case is preferably closed, as well. To change between said configurations, said main case is preferably opened temporarily.

If said clamping portion secures said sample acquisition portion, it applies a pressing force to an adequate section of said sample transfer member, at least if said sample acquisition portion is about to alter its current configuration. Depending on the tolerances chosen by a person skilled in the art in the mechanical design process based on the disclosure presented herein, limited movement can be allowed, as long as the current configuration persists.

Preferably, said clamping portion is designed to apply a pressing force permanently to an adequate section of said sample transfer member, if it secures said sample acquisition portion either in said sample acquisition configuration or in said sample transfer configuration. A pressing force to secure said sample acquisition portion in either configuration may be different and specific to each configuration.

Permanent application of said pressing force increases distinctness of the mechanical state of said sample transfer member in the respective configuration, in particular distinctness of the mechanical state of said sample acquisition portion. This increases security of handling the sampling device and acquiring and processing said liquid sample.

Said clamping portion and said sample transfer member are preferably designed so that said pressing force is encountered by a structural elastic force of said sample transfer member, if said sample acquisition portion is secured. This way, said sample transfer member structural elastically urges against said clamping portion and therefore has a distinct mechanical state.

Said main case can be a single part or preferably an assembly. In case of said assembly it can be permanently or reversibly assembled.

For reversible connections or assemblies, plug-in connections, latching, snapping or clipping connections and the like are preferred in the context of the invention. This allows for improved production and also disposal as said connections can be separated for recycling.

Said test strip mounting portion preferably has a number of holding structures, such as ribs for example, that are designed to hold a test strip. Thus, the test strip can be easily applied and removed, in case of recycling. However, said test strip mounting portion could also be implemented as a gluing surface for example.

Said indicator section preferably comprise a window through that a mounted test strip is visible. Said indicator section and said test strip mounting portion are adapted to each other, so that at least a result display area of a test strip, if mounted in said test strip mounting portion, is visible. Preferably, only said result display area is visible in said main case from outside.

In a preferred embodiment of the sampling device of the invention, said sample transfer member has a base portion and a sample handling portion that comprises said sample acquisition portion, wherein said sample handling portion and said base portion are designed as a serial kinematics and said base portion is connected to said main case within said clamping portion.

Such type of kinematics makes it easy to switch quickly between the different configurations and is achievable at low manufacturing effort.

Preferably, said sample handling portion comprises a pivoted extension of said base portion.

Further preferred, said sample handling portion comprises a sample handling arm with said sample acquisition portion and said base portion comprises a base arm, said sample handling arm and said base arm being connected by an integral hinge.

In other words, said sample transfer member preferably comprises a structure similar to a pair of compasses type of kinematics.

Such kinematics are especially suitable to realize said sample acquisition configuration and said sample transfer configuration.

Further, such structures can be easily manufactured and equipped with structural elastic properties as referred to above in the context of the pressing force.

For example, said sample handling arm and said base arm can be injection molded. For example, in the area of the desired integral hinge some material can be removed or a material strength can be reduced even in the injection molding process itself.

If some material is to be removed it can be stamped out, for example. For example, a pad can be applied to said sample handling arm forming said sample acquisition portion.

In a further preferred embodiment of the sampling device of the invention, in said sample acquisition configuration said serial kinematics is in an elongated condition while said clamping portion can be closed entirely, so that said sample acquisition portion is forming a rod-type structure with said main case.

In said elongated condition, said serial kinematics has similarity with a totally spread pair of compasses.

This makes it possible to use the sampling device of the invention like a rod or stick when applying it to the body providing said liquid sample. Doing so said clamping portion can be closed entirely, making it very safe and comfortable in use.

To close said clamping portion entirely, while said sample handling portion ranges out of said main case, a recess can be provided at a proximal end of said main case. Said recess remains, if said clamping portion is closed entirely.

For example, said sample handling portion, for example with said sample handling arm, can extend through said recess. In that case, said integral hinge remains located inside said main case to assure that said sample handling arm is forming said rod-type structure with said main case and is not pivoting or at least not pivoting out of defined tolerances while extending through said recess.

Said sample handling arm can have structurally elastic properties and urge against said recess driven by said elasticity, while extending through said recess. In that case, said structural elastic force referred to above preferably originates from said integral hinge.

In a further preferred embodiment of the sampling device of the invention, in said sample transfer configuration said serial kinematics is in a shortened condition while said clamping portion can be closed entirely, so that said sample acquisition portion is stored entirely within said main case.

In said shortened condition, said serial kinematics has similarity with a totally folded pair of compasses.

As said sample acquisition portion is stored entirely within said main case, no interaction between said liquid sample and the environment is possible. Said sampling device can be stored as a compact unit for later disposal or if said result shown by said test strip is to be inspected later on.

To switch between said elongated condition and said shortened condition, said serial kinematics can be manipulated manually. Additionally, said structural elastic force, if present, can support switching between said elongated condition and said shortened condition, as it can initially move said serial kinematics towards said sample transfer configuration. This significantly supports said manual manipulation.

In other words, said (so called) folded pair of compasses initially starts to fold up on its own, due to said elasticity, which makes it much easier to further fold it up entirely by hand.

Especially if said sample transfer member is connected to said main case by a pin connection, said hand manipulation can directly start in a direction that at least partially traverses a connecting direction of said pin connection and therefore prevents the pin connection from loosening.

In a further preferred embodiment of the sampling device of the invention, said clamping portion has a snap-fit, designed to reversibly secure said clamping portion once it has been closed entirely.

This way, even if said sample handling portion applies a structurally elastic force to said clamping portion, it remains securely closed, unless it is opened by additional manual manipulation. Said manipulation by hand can be applied to said clamping portion directly but also to said sample handling portion that pushes said clamping portion open due to said manipulation by hand.

In a further preferred embodiment of the sampling device of the invention, said clamping portion comprises a beak-like kinematics.

Such type of kinematics, known in concept for example from ducks or other birds, can be realized and used quite easily.

For example, said main case can have an upper case and a lower case. Said upper case can have a front section pivoting relatively to a back section. Said lower part can be a stiff structure.

Preferably, said front section is designed to pivot on said back section by means of an integral hinge.

In a further preferred embodiment of the sampling device of the invention, a strainer is located within said sample reception section, separating said strip mounting portion from said sample acquisition portion in said sample transfer configuration.

This way it is assured that only said liquid sample is applied to said strip mounting portion or in particular to a test strip if mounted therein. This assures that said test strip is not harmed mechanically by said sample acquisition portion. Still, in other embodiments, said test strip may be brought well in contact with said sample acquisition portion to be wet, if both components are designed for that purpose.

In the embodiment currently discussed, said liquid sample can be applied to said strip mounting portion in said sample reception section via said strainer. This can be realized by delayed off-dripping for example. This delayed off-dripping can happen automatically after a certain time period of can be initiated as said sample acquisition portion is wetting said strainer.

Said liquid sample then drips through said strainer or runs along said strainer. Said strainer can preferably have guiding blades to lead said liquid sample to said strip mounting portion or said test strip, respectively.

In a further preferred embodiment of the sampling device of the invention, in said sample transfer configuration said sample acquisition portion can be pressed against said strainer.

Thus, said liquid sample can be squeezed at least partially off said sample acquisition portion by said strainer, if pressed against.

It is mostly preferred, that said strainer is wetted by said sample acquisition portion and squeezes said sample acquisition portion, if pressed against it.

In a further preferred embodiment of the sampling device of the invention, said clamping portion is capable of pressing said sample acquisition portion against said strainer in said sample transfer configuration.

Preferably, said sample acquisition portion can be pressed against said strainer by said beak-like structure if it is closed.

In a further preferred embodiment of the sampling device of the invention, a pressing force applied to said sample acquisition portion ranges from 0.3 N to 10 N, if said clamping portion is closed entirely. Further preferred, said pressing force ranges from 0.3 N to 5N, further preferred from 0.3 N to 3 N, further preferred from 0.3 N to 2 N and even further preferred from 0.3 N to 1 N or from 1 N to 2 N.

Test runs done by the applicant have shown that said pressing force, if kept in said range allows for a high level of comfort and safe extraction of said liquid sample from said sample acquisition portion. The given values have turned out to be in particular suitable, if said liquid sample is a saliva sample. In case of said saliva sample a pressing force in said range of 0.3 N to 1 N or 1 N to 2 N has turned out to be most suitable, depending on the properties of said sample acquisition portion. If said sample acquisition portion comprises a pad, a range of 0.3 N to 1 N is preferred in case of a very soft pad, whereas a range of 1 N to 2 N is preferred in case of a common saliva pad.

In a further preferred embodiment of the sampling device of the invention, said strainer is comprised by a base portion of said sample transfer member.

This way, said strainer can be easily manufactured along with said sample transfer member. Said strainer can for example be integrated in an injection molding process. Said strainer can also be stamped out, for example.

Alternatively, said strainer can be comprised by said main case and can be manufactured integrally with said main case or permanently or reversibly assembled with said main case.

In a further preferred embodiment of the sampling device of the invention, said sample transfer member comprises a handling nipple designed to manipulate said sample transfer member.

Thus, especially if said liquid sample has already been acquired and applied to for example a pad of said sample transfer member, safety and comfort are increased significantly. Said handling nipple can be grabbed without interference of a user's hand with said liquid sample.

Preferably, said handling nipple is located on a side portion of said sample transfer member. This makes said handling nipple even accessible if said main case is closed, as it can extend out of said main case at a side.

Said handling nipple can be designed to open said clamping portion, if said clamping portion is closed and said handling nipple is then pushed upwards. This makes it easy to open said clamping portion on demand.

In a further preferred embodiment of the sampling device of the invention, a test strip is mounted in said test strip mounting portion.

Said test strip preferably ranges from said indicator section to said sample reception section. Preferably said test strip is running below said strainer in said sample reception section.

Another aspect of the invention refers to a reading device, comprising a mechanical interface designed to receive said sampling device of the invention according to the preceding description, said reading device further comprising a sensing unit capable of acquiring data from said indicator section of said sampling device, if said sampling device is applied to said mechanical interface.

Said reading device is designed to read a result displayed by said test strip. Since test strips often display a result encoded, for example barcode-like, said reading device is preferably capable of communicating said result to a user in a better understandable manner. For example, said result can be communicated verbally or by illustration, such as a pictogram or symbol.

Preferably, said sensing unit comprises an optical sensor.

Preferably, said reading device comprises means for wireless communication of said result. For example, said reading device can be configured to communicate said result to a smart device of a user.

Another aspect of the invention refers to a sampling system, comprising said sampling device of the invention according to the preceding description and said reading device of the invention according to the preceding description.

Specific Embodiments

Figure 1:
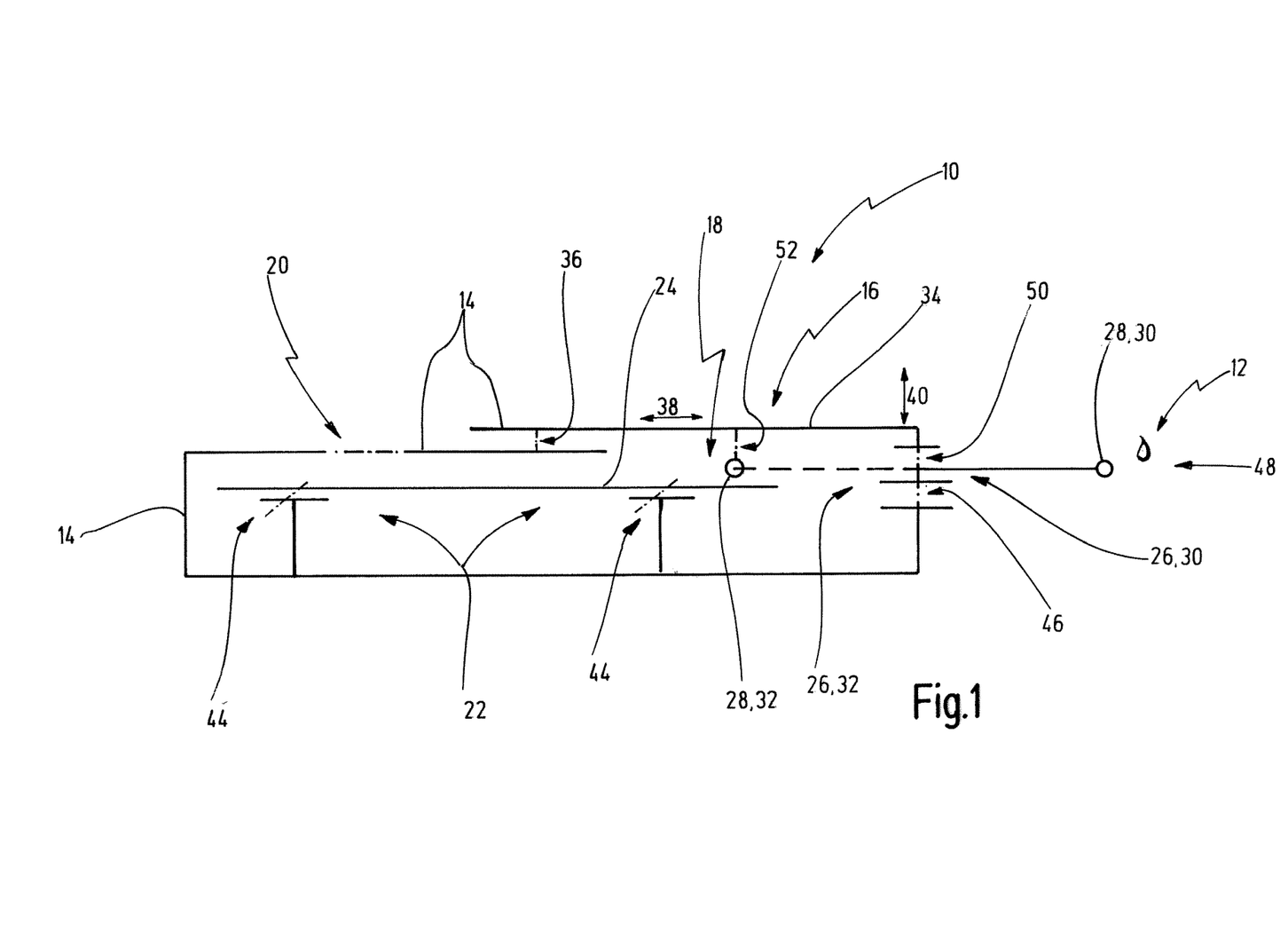
FIG. 1 shows a schematic diagram of a sampling device according to the invention.

Referring now to the Figures, FIG. 1 shows a sampling device 10 of the invention for a liquid sample 12. As FIG.

1 shows a schematic diagram it is not depending on a certain physical structure, but illustrates the functioning of said sampling device 10 in principle.

Said sampling device 10 comprises two major elements: a main case 14 and a sample transfer member 26.

Said main case 14 has a clamping portion 16 with a clamping element 34 that features an operative connection 36 to the rest of said main case 14. Due to said operative connection 36 said clamping element 34 is capable of performing a sliding movement 38 or a pivoting movement 40 relatively to said main case 14, for example.

Said main case 14 further has a sample reception section 18. Said sample reception section 18 is located within said clamping portion 16 and represents an area to that said liquid sample 12 is to be transferred.

Said main case 14 further has a test strip mounting portion 22 designed to have a test strip 24 mounted therein, which is illustrated by operative connection 44 between said test strip mounting portion 22 and said test strip 24.

Said main case 14 further has an indicator section 20.

Said test strip 24 is mountable in said test strip mounting portion 22 so that it extends into said sample reception section 18, as well as into said indicator section 20. Said test strip 24 is observable through said indicator section 20 to gather a result displayed by said test strip 24.

Said sample transfer member 26 is connected to said main case 14 by a permanent or temporary connection 46.

Said sample transfer member 26 has a sample acquisition portion 28, suitable to collect and transfer said liquid sample 12.

Said sample transfer member 26 and said main case 14 are configurable in a sample acquisition configuration 30. In said sample acquisition configuration 30, said sample acquisition portion 28 is located outside said main case 14. This is shown in FIG. 1 by a continuous line illustrating said sample transfer member 26 at a proximal end 48 of said sampling device 10.

In said sample acquisition configuration 30 said sample acquisition portion 28 is securable by said clamping portion 16.

For this purpose, said clamping portion 16 is designed to reversibly apply a pressing force to said main case 14 and/or to said sample transfer member 26, which is illustrated by operative connection 50.

Said sample transfer member 26 and said main case 14 are further configurable in a sample transfer configuration 32.

In said sample transfer configuration 32 said sample acquisition portion 28 is located within said sample reception section 18. This is shown in FIG. 1 by an interrupted line, illustrating said sample transfer member 26 in said sample reception section 18.

In said sample transfer configuration 32 said sample acquisition portion 28 is again securable by said clamping portion 16.

Or this purpose, said clamping portion 16 is designed to reversibly apply a pressing force to said main case 14 and/or to the sample transfer member 26, illustrated by said operative connection 50 and/or to apply a pressing force to said sample transfer member 26, illustrated by operative connection 52.

If said operative connection 50 and/or 52 is supposed to apply said pressing force via a sliding movement 38, a person skilled in the art knows adequate kinematic concepts to realize this function, such as the use of inclined planes or wedges moved along in said sliding movement 38.

If both, said liquid sample 12 and said test strip 24 are present in said sample reception section 18, said liquid sample 12 can be transferred to said test strip 24 and then be analyzed by said test strip 24. A result, displayed by said test strip 24, can then be gained from said indicator section 20.

Figure 2:
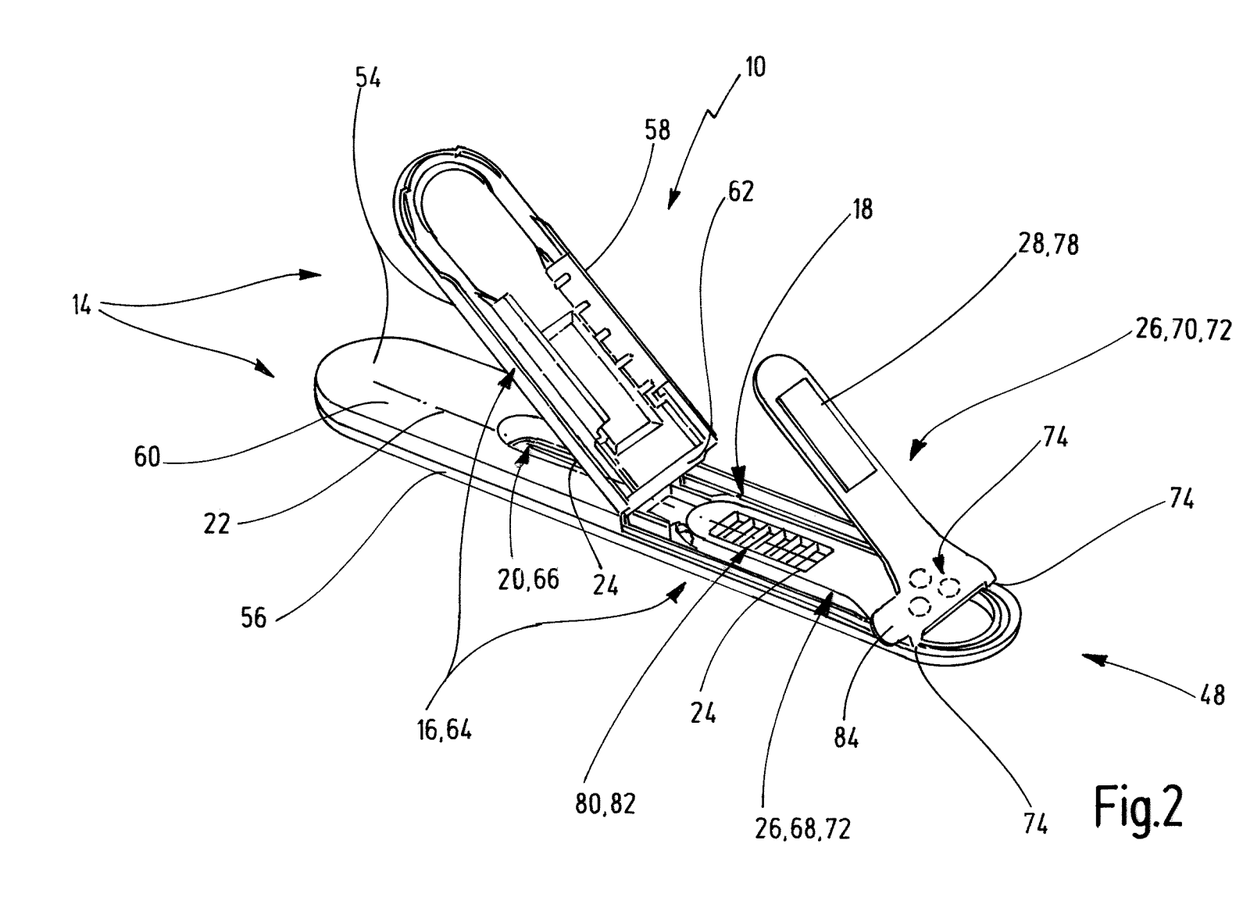
FIG. 2 shows a preferred embodiment of a sampling device according to the invention.

FIG. 2 shows a preferred embodiment of a sampling device 10 according to the invention. Said sampling device 10 implements the functions schematically described with regard to FIG. 1. Therefore, the reference signs of FIG. 1 are applicable for FIG. 2, as well. The embodiment of FIG. 2 additionally describes exemplary structure suitable to realize said sampling device 10 and to achieve said functions in a preferred manner.

Said sampling device 10 in FIG. 2 has a main case 14. Said main case 14 comprises an upper case 54 and a lower case 56. Said upper case 54 comprises a front section 58 and a back section 60. Said front section 58 is pivoted to said back section 60 by means of an integral hinge 62.

Said lower case 56 is a stiff structure. Thus, said pivoted front section 58 and said lower case 56 are forming a clamping portion 16 of said main case 14. Said clamping portion 16 has a beak-like kinematics 64.

In said back section 60, said upper case 54 comprises an indicator section 20 that is herein implemented as a window 66.

Said main case 14 further has a sample reception section 18. Said sample reception section 18 is located within said clamping portion 16.

Said main case 14 further has a test strip mounting portion 22 designed to have a test strip 24 mounted therein. In the shown embodiment, said test strip 24 is mounted in said test strip mounting portion 22. As can be seen, said test strip 24 extends into said indicator section 20 and from there no further in the direction of a proximal end 48 of said sampling device 10. Said test strip 24 further extends well into said sample reception section 18.

Now, a sample transfer member 26 comprised by said sampling device 10 will be described.

Said sample transfer member 26 has a base portion 68 and a sample handling portion 70. Said base portion 68 and said sample handling portion 70 are jointly designed as a serial kinematics 72. For that purpose, said sample transfer member 26 has an integral hinge 74 that connects said base portion 68 and said sample handling portion 70 in a way that said sample handling portion 70 is pivoted to said base portion 68.

Said base portion 68 is connected to said main case 14 within said clamping portion 14. Herein, said base portion 68 is connected to said lower case 56. In particular, said base portion 68 is connected to said lower case 56 by means of a pin connection 76, that is covered by said sample transfer member 26 in the given illustration of FIG. 2.

Further, said sample handling portion 70 comprises a sample acquisition portion 28. Said sample acquisition portion 28 is pivoted to said base portion 68 via said sample handling portion 70. Said sample acquisition portion 28 is suitable to collect said liquid sample 12, transfer said liquid sample 12 by temporarily binding of said liquid sample 12 and pivoting of said sample handling portion 70 and then at least partially releasing of said liquid sample 12. For example, said sample acquisition portion 28 can be implemented as a pad 78.

Further, said base portion 68 comprises a strainer 80 that is located within said sample reception section 18. In said sample reception section 18, said test strip 24 runs below said strainer 80 and said pad 78 can be brought in contact with said strainer 80.

Said strainer 78 comprises a plurality of guiding blades 82, making said test strip 24 accessible for said liquid sample 12 carried by said pad 78.

For the purpose of manual manipulation, said sample transfer member 26 can comprises a handling nipple 84.

Now, with regard to FIGS. 3 to 6, certain functions of said sampling device 10 of FIG. 2 are described in more detail. It shall be understood that the following description refers to exactly that sampling device 10 of FIG. 2, so that for the sake of illustration not all of the reference signs used in FIG. 2 are shown again.

Figure 3:
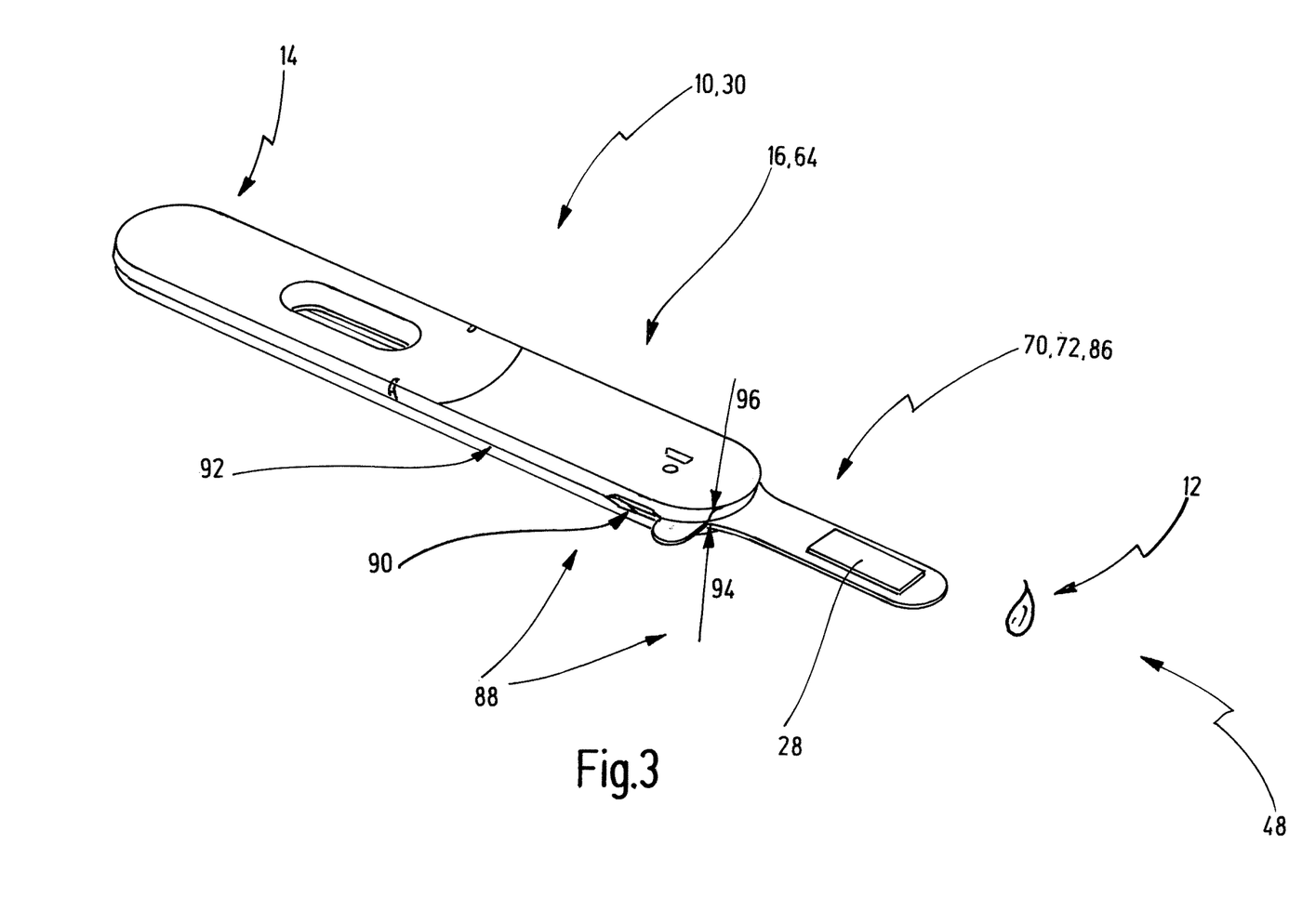
FIGS. 3-6 show functions of the sampling device of FIG. 2.

FIG. 3 shows said sampling device 10 in a sample acquisition configuration 30. At the proximal end 48 of said sampling device 10 said liquid sample 12 is illustrated.

Right next to said liquid sample 12, said serial kinematics 72 is illustrated in an elongated condition 86. While said serial kinematics 72 is in said elongated condition 86, said clamping portion 16 can be closed entirely. Comparison of said clamping portion 16 in FIGS. 2 and 3 underlines said beak-like kinematics 64.

In said sample acquisition configuration 30 as the shown in FIG. 3, with said clamping portion 16 being closed entirely said sample acquisition portion 28 is forming a rod-type structure 88 with said main case 14.

To have said sample acquisition portion 28 extending out of said main case 14, a recess 90 is provided in said main case 14 that remains even if said clamping portion 16 is closed entirely.

Said clamping portion 16 has a snap-fit 92, designed to reversibly secure said clamping portion 16 once it has been closed entirely.

While said clamping portion 16 is closed, said sample handling portion 70 urges against said recess 90 driven by a structural elastic force 94. Said structural elastic force 94 is created due to said integral hinge 72, in particular by structural elastic properties of a material of said integral hinge 72 that tend to keep said serial kinematics 72 not entirely in said elongated condition 86.

However, said clamping portion 16 secures said sample acquisition portion 28 in position by encountering said structural elastic force 94 by a pressing force 96. Herein, this pressing force 96 is first applied manually to close said clamping portion 16 and then kept up by said snap-fit 92.

Figure 4:
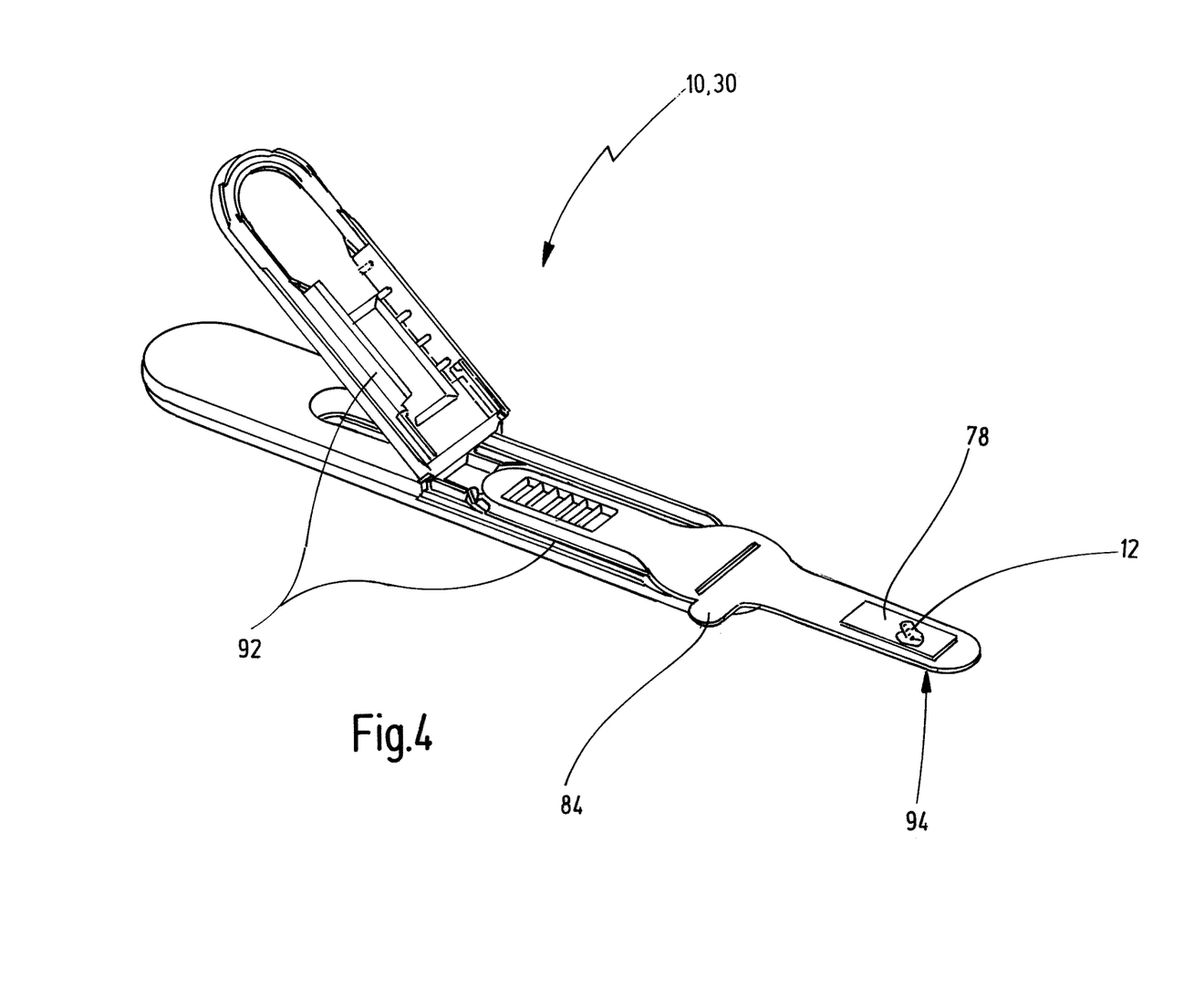

Now with regard to FIG. 4, said liquid sample 12 has been gathered by said pad 78. Said clamping portion 16 can be opened manually by overcoming said pressing force 96 kept up by said snap-fit 92.

Said pad 78 can now be pivoted in the direction of said structural elastic force 94. This can be supported by hand, for example grapping said handling nipple 84.

Figure 5:
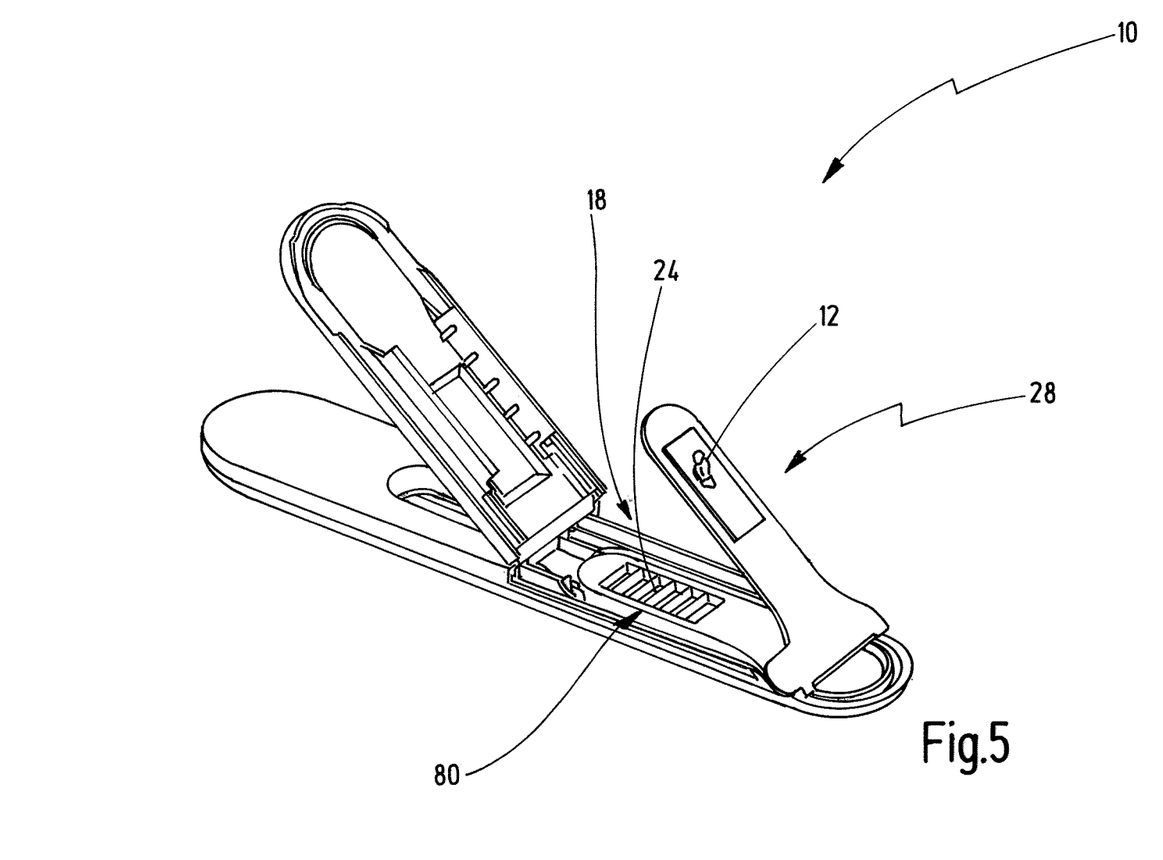

Now with regard to FIG. 5, said sampling device 10 is in-between said sample acquisition configuration 30 and a sample transfer configuration 32, as said sample acquisition portion 28 moves from outside of said main case 14 towards said sample reception section 18.

Once it reaches said sample transfer configuration 32, said sample acquisition portion 28 can come into contact with said strainer 80. Even though said strainer 80 separates said test strip 24 from said sample acquisition portion 28, it allows said liquid sample 12 to run through said strainer 80 in said sample transfer configuration 32 and reach said test strip 24. To support this process, said sample acquisition portion 28 can be pressed against said strainer 80, for example manually.

Figure 6:
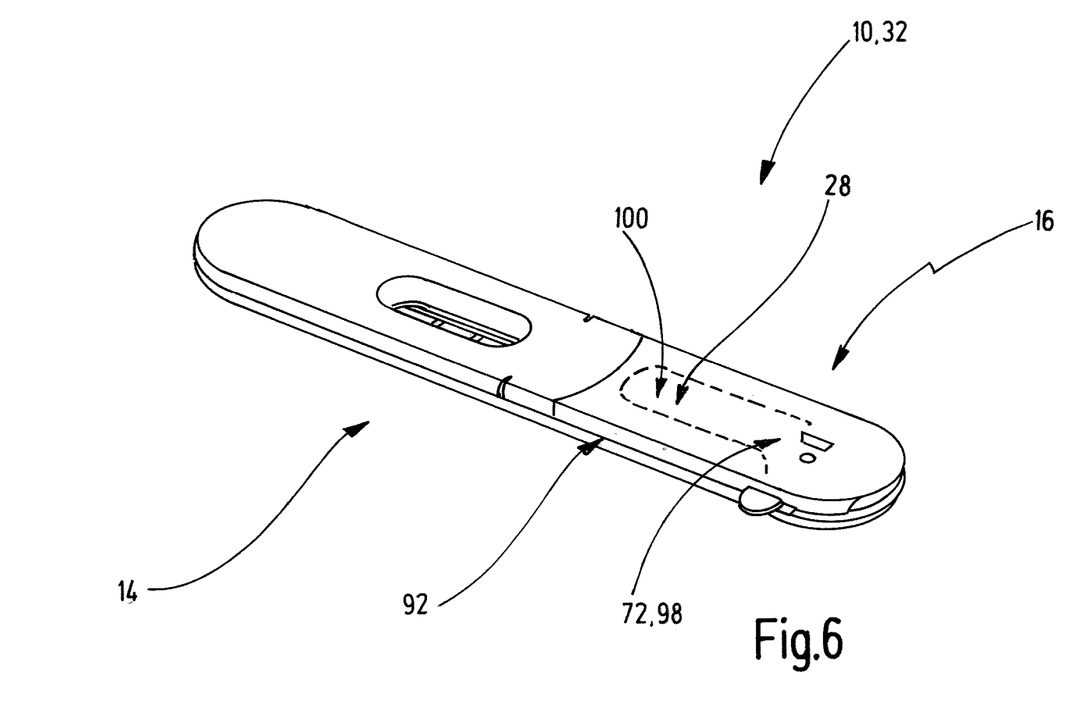

Said sample transfer configuration 32 is shown in FIG. 6. As can be seen, said sample acquisition portion 28 is now located within said sample reception section 18. This is achieved, as said serial kinematics 72 is now in a shortened condition 98.

In this state, said sample acquisition portion 28 is again secured by said clamping portion 16, that is closed entirely and thus entirely stores said sample acquisition portion 28 within said main case 14. To keep said clamping portion 16 closed entirely, said snap-fit 92 is engaged again.

As indicated, to support the process of transferring liquid sample 12 to said test strip 24, said sample acquisition portion 28 can be pressed against said strainer 80.

In said sample transfer configuration 32 said clamping portion 16 is capable of pressing said sample acquisition portion 28 against said strainer 80.

Preferably, said sample acquisition portion 28, said strainer 80 and said clamping portion 16 are designed so that said clamping portion 16 applies a pressing force 100 to said sample acquisition portion 28 that amounts to 1.5 N in this embodiment, if said clamping portion 16 is closed entirely.

Figure 7:
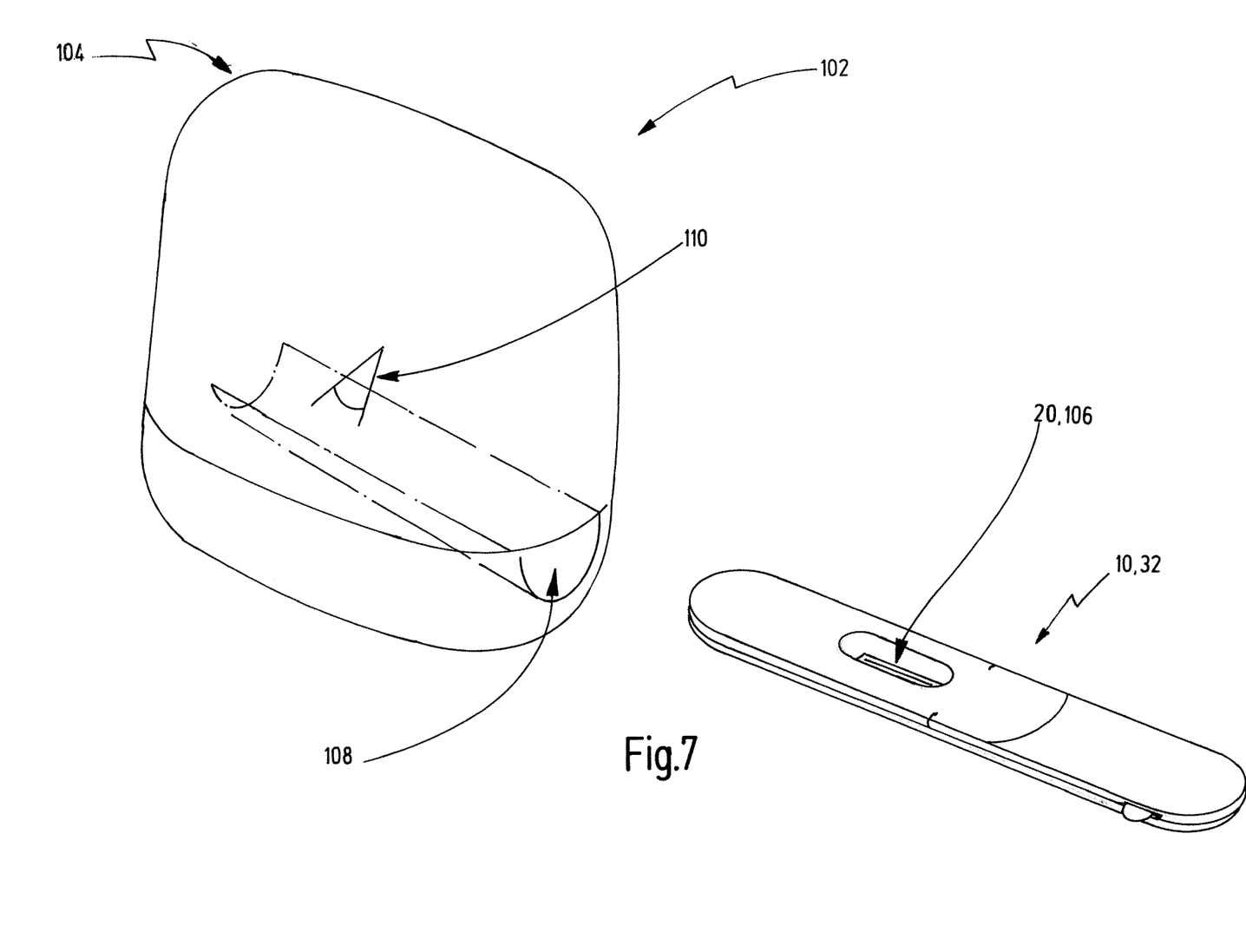
FIG. 7 shows a sampling device according to the invention and a reading device according to the invention in a sampling system according to the invention.

FIG. 7 shows a sampling system 102 according to the invention.

Said sampling system 102 comprises a sampling device 10 according to the invention, that is preferably designed as described above with regard to FIGS. 2 to 6. Accordingly, the same reference signs will be applied in FIG. 7. However, any other sampling device according to the invention is suitable for said sampling system 102.

Further, said sampling system 102 comprises a reading device 104 according to the invention.

The sampling device 10 shown is in said sample transfer configuration 32 and displays a result 106 in said indicator section 20.

Said reading device 104 comprising a mechanical interface 108 designed to receive said sampling device 10.

Said reading device 104 further comprising a sensing unit 110 capable of acquiring data from said indicator section 20, if said sampling device 10 is applied to said mechanical interface 108.

What is claimed is:

1. A sampling device for a liquid sample, the sampling device comprising:
   a) a main case having a clamping portion, a sample reception section and an indicator section, said sample reception section being located within said clamping portion, wherein said main case further has a test strip mounting portion configured to mount a test strip therein so that said test strip can extend into said sample reception section as well as said indicator section; and
   b) a sample transfer member being connected to said main case and having a sample acquisition portion, wherein said sample transfer member and said main case are configurable in at least the following configurations:
      i) a sample acquisition configuration, wherein said sample acquisition portion is located outside said main case and securable in said sample acquisition configuration by said clamping portion; and
      ii) a sample transfer configuration, wherein said sample acquisition portion is located within said sample reception section and securable in said sample transfer configuration by said clamping portion;
   wherein said sample transfer member comprises a handling nipple designed to manipulate said sample transfer member, wherein said handling nipple is located on a side portion of said sample transfer member;
   wherein said sample transfer member has an elongate shape, and wherein said sample transfer member, in its entirety except for the handling nipple, is enclosed collectively by said clamping portion and said sample reception section when in said sample transfer configuration.

2. A sampling device according to claim 1, wherein said sample transfer member has a base portion and a sample handling portion that comprises said sample acquisition portion, wherein said sample handling portion and said base portion are formed as a serial kinematics and said base portion is connected to said main case within said clamping portion.

3. A sampling device according to claim 2, wherein in said sample transfer configuration said serial kinematics is in a shortened condition, wherein said clamping portion is closed entirely.

4. A sampling device according to claim 2, wherein in said sample acquisition configuration said serial kinematics is in an elongated condition while said clamping portion is closed entirely, so that said sample acquisition portion is forming a rod-type structure with said main case.

5. A sampling device according to claim 4, wherein in said sample transfer configuration said serial kinematics is in a shortened condition while said clamping portion is closed entirely.

6. A sampling device according to claim 1, wherein said clamping portion has a snap-fit, configured to reversibly secure said clamping portion once said clamping portion has been closed entirely.

7. A sampling device according to claim 1, wherein said main case has an upper case and a lower case, and said upper case has a front section that is pivotable relative to a back section to form said clamping portion.

8. A sampling device according to claim 1, wherein a strainer is located within said sample reception section, separating said strip mounting portion from said sample acquisition portion in said sample transfer configuration.

9. A sampling device according to claim 8, wherein in said sample transfer configuration said sample acquisition portion is pressed against said strainer.

10. A sampling device according to claim 9, wherein said clamping portion presses said sample acquisition portion against said strainer in said sample transfer configuration.

11. A sampling device according to claim 10, wherein in said sample transfer configuration a pressing force is applied to said sample acquisition portion by the clamping portion that ranges from 0.3 N to 10 N.

12. A sampling device according to claim 8, wherein said strainer is comprised by a base portion of said sample transfer member.

13. A sampling device according to claim 1, wherein a test strip is mounted in said test strip mounting portion.

14. A sampling system comprising:
a sampling device according to claim 1; and
a reading device configured to receive the sampling device and including
a sensing unit configured to acquire data from an indicator section of said sampling device when said sampling device is received by said reading device.

15. A sampling device for a liquid sample, the sampling device comprising:

a) a main case having a clamping portion, a sample reception section and an indicator section, said sample reception section being located within said clamping portion, wherein said main case further has a test strip mounting portion configured to mount a test strip therein so that said test strip can extend into said sample reception section as well as said indicator section; and b) a sample transfer member being connected to said main case and having a sample acquisition portion, wherein said sample transfer member and said main case are configurable in at least the following configurations:
i) a sample acquisition configuration, wherein said sample acquisition portion is located outside said main case and securable in said sample acquisition configuration by said clamping portion; and
ii) a sample transfer configuration, wherein said sample acquisition portion is located within said sample reception section and securable in said sample transfer configuration by said clamping portion;
wherein said sample transfer member comprises a handling nipple designed to enable manipulation of said sample transfer member from said sample acquisition configuration to said sample transfer configuration by moving said sample acquisition portion into said sample reception section, wherein said handling nipple is located on a side portion of said sample transfer member;
wherein said sample transfer member has an elongate shape, and wherein said sample transfer member, in its entirety except for the handling nipple, is enclosed collectively by said clamping portion and said sample reception section when in said sample transfer configuration.

16. A sampling device according to claim 15, wherein said sample transfer member has a base portion and a sample handling portion that comprises said sample acquisition portion, wherein said sample handling portion and said base portion are formed as a serial kinematics and said base portion is connected to said main case within said clamping portion.

17. A sampling device according to claim 16, wherein in said sample transfer configuration said serial kinematics is in a shortened condition, wherein said clamping portion is closed entirely and said sample acquisition portion is stored entirely within said main case.

18. A sampling device according to claim 17, wherein:
in said sample acquisition configuration said serial kinematics is in an elongated condition while said clamping portion is closed entirely, so that said sample acquisition portion is forming a rod-type structure with said main case; and
in said sample transfer configuration said serial kinematics is in a shortened condition while said clamping portion is closed entirely, so that said sample acquisition portion is stored entirely within said main case.

19. A sampling device according to claim 18, wherein said clamping portion has a snap-fit, configured to reversibly secure said clamping portion once said clamping portion has been closed entirely.

* * * * *